United States Patent [19]

Baker et al.

[11] Patent Number: 4,996,211

[45] Date of Patent: Feb. 26, 1991

[54] SUBSTITUTED DIBENZOCYCLOHEPTENIMINES

[75] Inventors: Raymond Baker, Much Hadham; Paul D. Leeson, Cambridge, both of England; Susan F. Britcher, Norristown, Pa.

[73] Assignee: Merck Sharp & Dohme Ltd., Hoddesdon, England

[21] Appl. No.: 231,295

[22] Filed: Aug. 12, 1988

[30] Foreign Application Priority Data

Aug. 13, 1987 [GB] United Kingdom ............... 8719199

[51] Int. Cl.$^5$ .................... C07D 221/22; A61K 31/44
[52] U.S. Cl. ...................... 514/289; 548/43; 548/72
[58] Field of Search ...................... 546/72, 43; 514/289

[56] References Cited

U.S. PATENT DOCUMENTS 3,892,756  7/1975  Nedelec et al. .................. 546/72
4,399,141  8/1983  Anderson et al. ............... 546/72 X

FOREIGN PATENT DOCUMENTS 0091071  10/1983  European Pat. Off. ........... 546/72
0230370   7/1987  European Pat. Off. .
0264183   4/1988  European Pat. Off. ........... 546/72
0303512   2/1989  European Pat. Off. ........... 546/72
7312616  10/1974  France ............................... 514/289

Primary Examiner—Mukund J. Shah
Assistant Examiner—E. C. Ward
Attorney, Agent, or Firm—Joseph F. DiPrima; Manfred Polk

[57] ABSTRACT

The present invention provides a compound of formula (I):

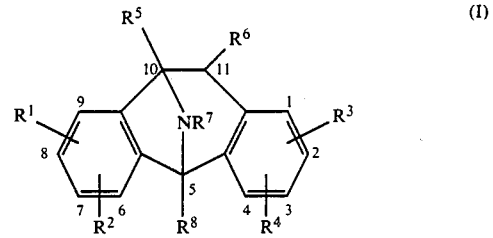

or a pharmaceutically acceptable salt thereof, wherein one of $R^1$, $R^2$, $R^3$ and $R^4$ represents a hydrocarbon or hydrocarbyloxycarbonyl group and the remaining groups $R^1$, $R^2$, $R^3$ and $R^4$ independently represent hydrogen, hydrocarbon, hydrocarbyloxycarbonyl, halogen, hydroxy or $C_{1-6}$ alkoxy, or $R^1$ and $R^2$ or $R^3$ and $R^4$ may together represent the residue of a carbocyclic ring; $R^5$ and $R^6$ independently represent hydrogen, hydrocarbon, hydroxy or fluoro; $R^7$ represents hydrogen or $C_{1-3}$ alkyl; and $R^8$ represents methyl or ethyl; which compounds are useful as anticonvulsant agents and in the treatment of neurodegenerative diseases.

11 Claims, No Drawings

SUBSTITUTED DIBENZOCYCLOHEPTENIMINES

This invention relates to a class of dibenzocycloheptenimines, and in particular to derivatives of 5-methyl-10,11-dihydro-5H-dibenzo[a,d]-cyclohepten-5,10-imine substituted with a hydrocarbon or hydrocarbyloxycarbonyl group. The compounds are useful as anticonvulsant agents and in the treatment of neurodegenerative diseases.

British Patent No. 2,004,872 (and U.S. Pat. No. 4,399,141) describes 5-methyl-10,11-dihydro-5H-dibenzo[a,d]and derivatives thereof as anticonvulsant agents. The use of those compounds as non-competitive N-methyl-D-aspartate (NMDA) receptor antagonists, and therefore their value in the treatment of neurodegenerative diseases, is disclosed in European patent application, publication No. 230370.

It has now been found that derivatives substituted with a hydrocarbon or hydrocarbyloxycarbonyl group on the benzo ring are also good anticonvulsants and NMDA receptor antagonists. None of the prior documents discloses or suggests hydrocarbon or hydrocarbyloxycarbonyl substituents at that position. The compounds of this invention are useful in the prevention and/or treatment of neurodegeneration in pathological conditions such as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Olivo-pontocerebellar atrophy, anoxia such as from drowning, spinal cord injury and poisoning by exogeneous NMDA poisons (e.g. some forms of lathyrism).

The present invention provides a compound of formula (I):

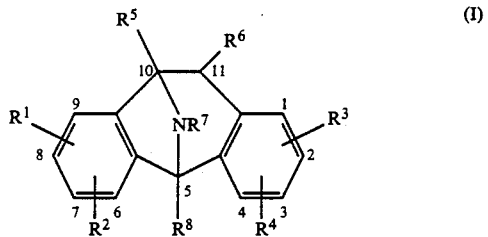

(I)

or a pharmaceutically acceptable salt thereof, wherein one of $R^1$, $R^2$, $R^3$ and $R^4$ represents a hydrocarbon or hydrocarbyloxycarbonyl group and the remaining groups $R^1$, $R^2$, $R^3$ and $R^4$ independently represent hydrogen, hydrocarbon, hydrocarbyloxycarbonyl, halogen, hydroxy or $C_{1-6}$ alkoxy, or $R^1$ and $R^2$ or $R^3$ and $R^4$ may together represent the residue of a carbocyclic ring; $R^5$ and $R^6$ independently represent hydrogen, hydrocarbon, hydroxy or fluoro; $R^7$ represents hydrogen or $C_{1-3}$ alkyl; and $R^8$ represents methyl or ethyl.

The term 'hydrocarbon' includes groups having up to 18 carbon atoms, suitably up to 10 carbon atoms, conveniently up to 6 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, and aryl($C_{1-6}$)alkyl.

The term 'hydrocarbyloxycarbonyl' as used herein refers to a group of formula $-CO_2R$ in which R represents a hydrocarbon group as defined above.

Suitable alkyl groups include straight and branched chain alkyl groups containing from 1 to 6 carbon atoms, such as methyl, ethyl, propyl and butyl. A particular alkyl group is methyl.

When used herein the term 'aryl' includes optionally substituted phenyl and naphthyl.

Any of the hydrocarbon groups may be substituted with a group selected from halogen, $C_{1-6}$ alkyl, phenyl, $C_{1-6}$ alkoxy, halo($C_{1-6}$)alkyl, hydroxy, amino, nitro, cyano, carboxy, $C_{1-6}$ alkoxycarbonyl, $C_{1-6}$ alkoxycarbonyl($C_{1-6}$)alkyl, $C_{1-6}$ alkylcarbonyloxy and $C_{1-6}$ alkylcarbonyl, and groups of formula $-CONR^aR^b$ and $-N-R^a.COR^b$ in which $R^a$ and $R^b$ independently represent hydrogen or hydrocarbon. Preferred substituent groups include halogen, hydroxy, $C_{1-6}$ alkyl, $C_{1-6}$ alkoxy and $C_{1-6}$ alkoxycarbonyl.

Suitable aryl groups include phenyl and chlorophenyl.

Suitable aryl($C_{1-6}$)alkyl groups are benzyl and chlorobenzyl.

Preferably $R^7$ represents hydrogen and $R^8$ represents methyl.

When $R^1$ and $R^2$ or $R^3$ and $R^4$ together represent the residue of a carbocyclic ring, the ring may be saturated or unsaturated. The $R^1/R^2$ or $R^3/R^4$ carbon chain may comprise from 2 to 6 carbon atoms, preferably 3 or 4 carbon atoms, i.e. forming a fused 5- or 6-membered ring, such as benzo.

In a preferred subgroup of compounds of formula (I), one of $R^1$ to $R^4$ represents $C_{1-6}$ alkyl, hydroxy($C_{1-6}$)alkyl, phenyl or $C_{1-6}$ alkoxycarbonyl, and the remaining groups $R^1$ to $R^4$ represent hydrogen or halogen, in particular chloro or bromo. It is also preferred that $R^5$ represents hydrogen, hydroxy or methyl and $R^6$ represents hydrogen or hydroxy, in particular exo-hydroxy.

The hydrocarbon or hydrocarbyloxycarbonyl group, $R^1$ to $R^4$, may be present at any position of the benzo rings, suitably at positions 2, 3, 4, 6, 7 or 8, in particular at positions 2, 3, 7 or 8. Hydrocarbon or hydrocarbyloxycarbonyl substitution at positions 3 and 7 leads to preferred compounds.

Particular compounds of this invention include:
5,7-dimethyl-10,11-dihydro-5H-dibenzo[a,d]cyclohepten-5,10-imine;
5,9-dimethyl-10,11-dihydro-5H-dibenzo[a,d]cyclohepten-5,10-imine;
3,5-dimethyl-10,11-dihydro-5H-dibenzo[a,d]cyclohepten-5,10-imine;
1,5-dimethyl-10,11-dihydro-5H-dibenzo[a,d]cyclohepten-5,10-imine;
5-methyl-3-phenyl-10,11-dihydro-5H-dibenzo[a,d]cyclohepten-5,10-imine;
7-methyl-12,13-dihydro-7H-benzo[4,5]cyclohepta[12-a]naphthalen-7,12-imine;
7-methyl-12,13-dihydro-7H-benzo[4,5]cyclohepta[12-a]naphthalen-7,13-imine;
2,5-dimethyl-10,11-dihydro-5H-dibenzo[a,d]cyclohepten-5,10-imine;
5,8-dimethyl-10,11-dihydro-5H-dibenzo[a,d]cyclohepten-5,10-imine;
3-methoxycarbonyl-5-methyl-10,11-dihydro-5H-dibenzo[a,d]cyclohepten-5,10-imine;
3-hydroxymethyl-5-methyl-10,11-dihydro-5H-dibenzo[a,d]cyclohepten-5,10-imine;
and salts thereof.

Suitable acid addition salts of compounds of this invention include pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methanesulphonate, α-ketoglutarate, α-glycerophosphate, and glucose-1-phosphate. Preferably the acid addition salt is a hemisuccinate, hydrochloride, α-ketoglutarate, α-glycerophosphate or glucose-1-phosphate, in particular the hydrochloride salt.

Also included within the scope of the present invention are pharmaceutical compositions comprising the imines of this invention. Preferably these compositions are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of an imine of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil and peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, and gelatine.

The novel imines of this invention are useful as anticonvulsants at a dosage level of from about 0.01 to about 20 mg per kilogram of body weight, preferably about 0.05 to 2 mg/kg of body weight, on a regimen of 1 to 4 times a day.

In the treatment of neurodegeneration, a suitable dosage level is about 0.01 to 50 mg/kg, preferably about 0.05 to 10 mg/kg and especially about 0.05 to 0.5 mg/kg/day. The compounds may be administered on a regimen of 1 to 4 times per day.

The compounds of this invention wherein $R^5$ is hydrogen or hydrocarbon and $R^6$ is hydrogen may be prepared by a process which comprises reducing the N-hydroxy compound of formula (II):

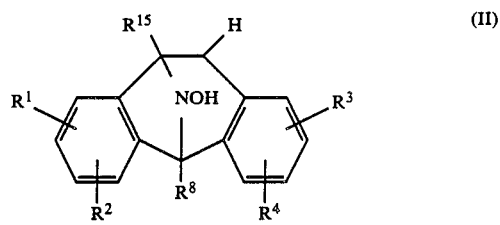

wherein $R^1$ to $R^4$ and $R^8$ are as defined with respect to formula (I) above and $R^{15}$ represents hydrogen or hydrocarbon; and, when $R^7$ is other than hydrogen, alkylation of the product. The preferred reducing agent is nascent hydrogen generated by the action of a metal, preferably zinc, with an acid, such as acetic acid. Suitable conditions for the process are a temperature of from 40° C. to 100° C. for 1 to about 10 hours.

The intermediate compounds of formula (II) may be prepared by the cyclisation of a compound of formula (III):

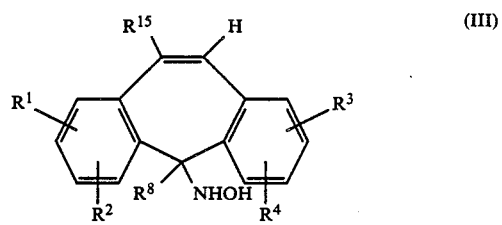

wherein $R^1$ to $R^4$ and $R^8$ are as defined with respect to formula (I) above and $R^{15}$ is as defined with respect to formula (II) above. The conditions for this reaction are elevated temperature or the presence of a base and are generally as described in U.S. Pat. No. 4477668. Both compounds (II) and (III) are novel compounds and represent further aspects of this invention. The compound (II) may also be prepared by processes analogous to those described in U.S. Pat. Nos. 4399141 and 4232158.

The novel compounds of this invention wherein $R^8$ represents a group of formula —CH$_2$R$^9$, in which $R^9$ is hydrogen or methyl, may also be prepared by ring closure of a 10-NHX-5-(=CHR$^9$)-10,11-dihydro-5H-dibenzo[a,d]cycloheptene (where X is the group $R^7$ or a protecting group, such as acetyl) by treatment with a strong base such as an organometallic reagent, for example n-butyllithium, in an ethereal solvent such as tetrahydrofuran or 1,2-dimethoxyethane, at about 0° C. to about 30° C. for about 5 minutes to about 1 hour, followed if necessary by removal of the protecting group.

The compounds of formula (I) in which at least one of $R^1$ to $R^4$ represents a hydrocarbon group may be prepared, where appropriate, by alkylation or arylation, i.e. by reaction of a compound of formula (IV):

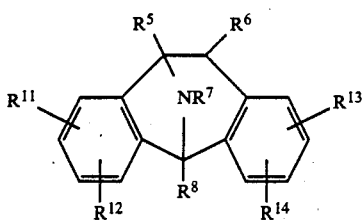

(IV)

wherein $R^5$ to $R^8$ are as defined with respect to formula (I) above, one of $R^{11}$, $R^{12}$, $R^{13}$ and $R^{14}$ represents halogen, and the remaining groups $R^{11}$, $R^{12}$, $R^{13}$ and $R^{14}$ independently represent hydrogen, hydrocarbon, halogen, hydroxy or $C_{1-6}$ alkoxy; with a reagent which replaces halogen by hydrocarbon. For example, a Grignard reagent such as an alkyl- or arylmagnesium bromide may be employed in the presence of a catalyst such as 1,3-bis(diphenylphosphino)propane nickel(II) chloride. If the hydrocarbon substituent is phenyl, a suitable reagent is $PhB(OH)_2/(PPh_3)_4Pd$ [phenyl boronic acid/tetrakis(triphenylphosphine)palladium].

The compounds of formula (I) in which at least one of $R^1$ to $R^4$ represents a hydrocarbyloxycarbonyl group may conveniently be prepared by metalation of a compound of formula (IV) as defined above with, for example, n-butyllithium; treatment of the resulting anion in situ with carbon dioxide; and subsequent esterification of the resulting carboxylic acid by standard means, such as by treatment with boron trifluoride etherate in the presence of a suitable alcohol.

Where appropriate, a compound of formula (I) initially obtained may subsequently be elaborated into a further compound of formula (I) as defined above. For example, a compound of formula (I) wherein one or more of $R^1$ to $R^4$ is/are hydroxymethyl may conveniently be obtained from the corresponding compound of formula (I) wherein one or more of $R^1$ to $R^4$ is/are hydrocarbyloxycarbonyl by treatment of the latter with a suitable reducing agent, e.g. lithium aluminium hydride.

The compounds of formula (I) in which $R^5$ represents hydroxy may be prepared by methods analogous to those described in EP-A-0264183. A further method is to treat the N-hydroxy compound of formula (II) above, in which $R^{15}$ is hydrogen, with manganese acetate, and subsequently to reduce the product thereby obtained with, for example, zinc in acetic acid. This method may be illustrated by the following scheme:

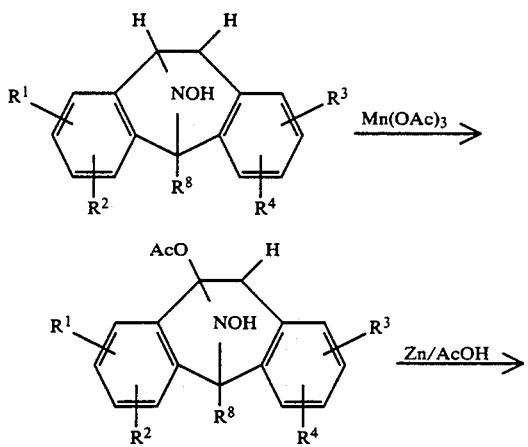

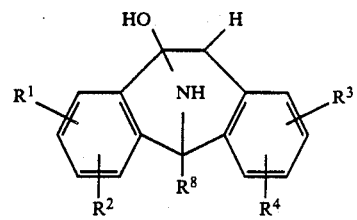

When it is desired that $R^7$ should be other than hydrogen, the resulting product can subsequently be alkylated.

The compounds of formula (I) in which $R^6$ represents hydroxy may be prepared by reducing an 11-oxo compound, in which the nitrogen atom may be protected. The reduction may be effected by treatment with, for example, diisobutylaluminium hydride (Dibal-H) in an ethereal solvent such as ether, tetrahydrofuran or 1,2-dimethoxyethane at about $-90°$ to $-60°$ C., preferably about $-78°$ C., for about 1 to 3 hours.

This process produces a mixture of endo and exo hydroxy derivatives which, after deprotection, may be separated by conventional techniques such as preparative chromatography. Alternatively, in order to obtain the 11-hydroxy compound selectively as its desired exo or endo isomer, the 11-oxo compound may be reduced with a chiral reducing agent such as D- or L-Selectride. Thus, it will be appreciated that a mixture of the exo and endo isomers ca be converted into a single desired exo or endo isomer by oxidation to the 11-oxo compound and subsequent application of the foregoing selective reduction technique. This approach can equally be adopted for the conversion of a single exo or endo isomer into the opposite isomer.

Further illustrative methods of preparing the exo and endo isomers of the 11-hydroxy compound selectively are described in EP-A-0264183.

The 10-fluoro derivative of compound (I) may be prepared by treating the corresponding 10-hydroxy compound with diethylaminosulphur trifluoride (DAST) in an inert organic solvent such as a chlorinated hydrocarbon such as chloroform or methylene dichloride at about 15° to 30° C. for about 30 minutes to 2 hours.

The isomeric 11-fluoro compound may be prepared by treating the aziridine of formula (V):

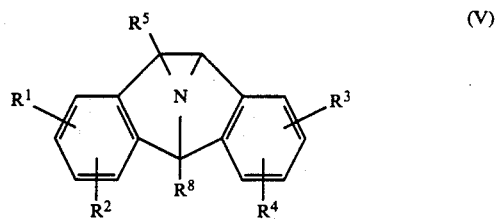

wherein $R^1$ to $R^5$ and $R^8$ are as defined with respect to formula (I) above; with hydrogen fluoride-pyridine (HF-70%; pyridine-30%) at about $-90°$ to $-60°$ C., preferably about $-78°$ C, followed by spontaneous warming to ambient temperature (15° to 30° C.) for about 12 to 36 hours.

During any of the above reactions it may be necessary to protect any reactive groups on any of the molecules concerned with conventional protecting groups which may subsequently be removed using methods known from the art.

The compounds useful in this invention bind with a high affinity and in a reversible and saturable manner to membranes from rat brain cortex. In addition these compounds potently and selectively block responses to NMDA in a brain slice from rat cortex, and antagonise NMDA-induced seizures in the mouse.

Binding Studies

The compounds of the invention were tested for their ability to displace a standard compound from rat brain. The standard compound employed is 5-methyl-10,11-dihydro-5H-dibenzo[a,d]cyclohepten-5,10-imine, hereinafter referred to as MK-801.

Binding of [$^3$H]-MK-801 to rat brain in vitro was conducted in a crude synaptosomal membrane fraction (P2) prepared from rat cerebral cortex according to a modified method of Hulme et al., *Molecular Pharmacology*, 1978, 14, 737-750. Compounds of the invention displaced the [$^3$H]-MK-801 binding in a concentration-dependent manner. The concentrations of the compounds of accompanying Examples 1 to 12 required to displace 50% of specific [$^3$H]-MK-801 binding (IC$_{50}$) were below 10 μM in each case.

Cortical Slice Studies

The effects of compounds of the invention on responses to NMDA were assessed using the rat cortical slice as described by Wong et al, *Proc. Natl. Acad. Sci. USA*, 1986, 83, 7104. The apparent equilibrium constant (K$_b$) was calculated from the righthand shift in the NMDA concentration-response curve produced by the compound under test. The compounds of accompanying Examples 1 to 6, 8 to 10 and 12 were tested and their K$_b$ values were found to be below 5 μM in each case.

Antagonism of NMDLA-induced seizures

Compounds of the invention were examined for their ability to antagonise tonic seizures induced by N-methyl-DL-aspartic acid (NMDLA). Groups of 8 male Swiss-Webster mice (25-30 g) were injected intravenously with the test compound at various doses, 15 min before s.c. administration of NMDLA (500 mg/kg). Animals were observed for the following 30 min and the number of mice protected from tonic extension of the forelimbs noted. ED$_{50}$ values for the antagonism of the NMDLA induced tonic seizures were determined using probit analysis. The compounds of accompanying Examples 1, 2, 5, 6 and 12 were tested and their ED$_{50}$ values were found to be below 10 mg/kg in each case.

The following Examples illustrate the preparation of compounds of this invention:

EXAMPLE 1

5,7-Dimethyl-10.11-dihydro-5H-dibenzo[a,d]cyclohepten-5,10-imine.

Step A: Preparation of 2-(2-(4-methylphenyl)ethyl)benzoic acid.

1,5-Diazabicyclo[4.3.0]non-5-ene (29.1 g) was added to a solution of 2-(carbomethoxy)benzyl triphenylphosphonium bromide (100 g) and p-tolualdehyde (26.7 g) in acetonitrile (250 ml). The mixture was refluxed for 10 minutes, the solvents removed in vacuo and the residue dissolved in chloroform (200 ml). Washed with 1N aqueous hydrochloric acid (100ml) and water (100 ml), then dried over sodium sulphate filtered and evaporated. The residue was refluxed overniqht in water (250 ml) and methanol (100 ml) containing potassium hydroxide (56 g). then cooled diluted with water (250 ml) and washed with chloroform (3×250 ml). The aqueous solution was acidified to pH 2 with conc. hydrochloric acid, and extracted with chloroform (3×200 ml). The extract was washed dried and evaporated to afford 2-carboxy-4'-methyl stilbene (44.2 g) as a cis- trans mixture. This mixture was hydrogenated in dimethylformamide (50 ml) at 50 psi in the presence of 10% palladium on charcoal catalyst (2 g). The catalyst was removed by filtration and solvent evaporated. The residue Was dissolved in ether, ,washed with water, dried and filtered to afford after evaporation and hexane trituration. 2-(2-(4-methylphenyl)ethyl)benzoic acid (40.0 g). m.p. 80°-82° C.

Step B: Preparation of 3-methyl-10,11-dihydro-5H-dibenzo[a,d]cyclohepten-5-one.

The acid from Step A (37.5 g) in sulfolane (200 ml) was heated to 110° C. and polyphosphoric acid (150 ml) added. After 1.5 hr at 110° C. the mixture was poured into water (500ml). extracted with hexane (3×200 ml) and the extract washed, dried, diluted with an equal volume of ether and percolated through silica (200 g). The eluate Was evaporated to afford 3-methyl-10,11-dihydro-5H-dibenzo[a,d]cyclohepten-5-one (30.5 g) as an oil. 60MHz NMR in deuterochloroform 2.35 (CH$_3$), 3.20 ppm [(CH$_2$)$_2$].

Step C: Preparation of 3-methyl-5H-dibenzo[a,d]cyclohepten-5-one.

The ketone from Step B (30.25 g) and N-bromosuccinimide (29.1 g) were refluxed in carbon tetrachloride (300 ml) for 5 hrs. The solution was cooled, filtered and evaporated and the residue dissolved in dimethylformamide (100 ml) and 1,5-diazabicyclo[4.3.0]non-5-ene (22 g) added. The solution was heated to 80° for 20 mins, then poured into water (300 ml) and extracted with ether (3×300 ml). The extract was washed with dilute aqueous hydrochloric acid and water, then dried and evaporated. Crystallisation from acetone/hexane gave pure 3-methyl-5H-dibenzo[a,d]cyclohepten-5-one (22.2 g). m.p. 81°-83° C.

Step D: Preparation of 3,5-dimethyl-5H-dibenzo [a,d]cyclohepten-5-ol.

To a solution of the ketone from Step C (22 g) in dry tetrahydrofuran (400 ml) at 0° C. under nitrogen was added a solution of methyl lithium in diethyl ether (100 ml of 1.4M). The solution was stirred for 1 hr at 0° C. then water was cautiously added and solvents evaporated to give an aqueous mixture which was extracted with ether (2×150 ml). The combined extracts were washed with water, dried and evaporated. Crystallisation from ether/hexane gave 3,5-dimethyl-5H-dibenzo[a,d]cyclohepten-5-ol (20.18 g), m.p. 102°-103° C.

Step E: Preparation of 3,5-dimethyl-5H-dibenzocyclohepten-5-hydroxylamine.

To a refluxing, vigorously stirred suspension of the carbinol from step D (5 g). anhydrous sodium acetate (17.37 g) and hydroXylamine hydrochloride (14.6 g) in dichloromethane (50 ml) was added dropwise, dichloroacetic acid (15 ml in 50 ml dichloromethane). The reaction was followed by TLC on silica in 1:1 ethyl acetate/hexane. The mixture was cooled, washed with 2N aqueous sodium hydroxide, (2×50 ml), water (50 ml). then dried and evaporated. Trituration with 1:1 ether/hexane gave 3.5-dimethyl-5H-dibenzo[a,d]cyclohepten-5-hydroxylamine (4.92 g). m.p. 142°-144° C.

Step F: Preparation of a mixture of 3- and 7-methyl-5-methyl-12-hydroxy-10,11-dihydro-5H-dibenzo [a,d]cyclohepten-5,10-imines.

To xylene (50 ml) at reflux was added over a 20 minute period, a solution of the hydroxylamine from Step E (1 g) in xylene (100 ml) under nitrogen. The solution was refluxed a further 10 minutes, then cooled, evaporated on silica using 2:3 ethyl acetate/hexane eluant to give the product mixture (520 mg), as a buff solid, m.p. 125°–130° C. Two pairs of atropisomers in the ratio 2:1 were evident in the 360 MHz $^1$H nmr spectrum.

Step G: Preparation of a mixture of 3- and 7-methyl-5-methyl-10,11-dihydro-(5H)-dibenzo[a,d]cycloheptenimines.

To a solution of the mixture from Step F (500 mg) in glacial acetic acid (5 ml) was added zinc powder (600 mg) and the mixture stirred at 65° C. for 3 hrs. A further 200 mg zinc was added and the mixture heated a further 1 hr. The mixture was filtered, the cake washed with acetic acid and solvents evaporated. The residue was partitioned between 2N aqueous sodium hydroxide and ether, the organic layer separated, washed with water, dried and evaporated then chromatographed on silica using chloroform eluant to afford a mixture of 3- and 7-methyl compounds as an oil (270 mg). Rf 0.31 on silica in 5% methanol/chloroform.

Step H: Preparation and separation of a mixture of 3- and 7-methyl-5-methyl-12-tert-butoxycarbonyl-10,11-dihydro-(5H)-dibenzo[a,d]cyclohepten-5,10-imines.

To a solution of the mixture of 3- and 7-methyl compounds from Step G (250 mg) in dichloromethane (2 ml) was added t-butylpyrocarbonate (327 mg) and triethylamine (152 mg). and the solution stirred at room temperature for 0.5 hr. The solution was evaporated to dryness and the residue partitioned between ether and water. The water was discarded and the ether layer dried and evaporated to give an oil which was chromatographed on a Lobar silica column using 1% ethyl acetate/hexane as eluent. Fractions were analysed by HPLC using 2% ethyl acetate/hexane. Isomers A (20 mg) and B (90 mg) were collected.

Step I: Preparation of 5.7-dimethyl-10,11-dihydro-5H-dibenzo[a,d]cyclohepten-5,10-imine hydrochloride.

To a solution of isomer B (90 mg) from step G in dry ethyl acetate (1 ml) was added hydrogen chloride gas in ethyl acetate (5.5M 1 ml) and the solution stirred for 0.5 hr. Evaporation and crystallisation from methanol/ether gave 5,7-dimethyl-10,11-dihydro5H-dibenzo[a,d]cyclohepten-5,10-imine hydrochloride (32 mg), mp 275°–280° C. Contamination with 3-isomer<5% by HPLC. The structure was confirmed as the 7-methyl isomer by $^1$H nmr spectroscopy.

EXAMPLE 2

3.5-Dimethyl-10,11-dihYdro-5H-dibenzo[a,d]cyclohepten-5,10-imine.

To a solution of isomer A (20 mg) from Example 1 (H) above, in dry ethyl acetate (0.5 ml) was added hydrogen chloride gas in ethyl acetate (5.5M, 0.5 ml) and the solution stirred for 0.5 hr. Evaporation and crystallisation from methanol/diethylether gave 3,5-dimethyl-5H-dibenzo[a,d]cyclohepten-5,10-imine hydrochloride (9.2 mg). Contamination with 7-isomer<5% by HPLC. The structure was confirmed as the 3 isomer by $^1$H nmr spectroscopy.

EXAMPLE 3

5,9-Dimethyl-10,11-dihydro-5H-dibenzo[a,d]cyclohepten-5,10-imine.

Step A: Preparation of 2-[2-(2-methylphenyl)ethyl]-benzoic acid.

Prepared from o-tolualdehyde as described in Example 1A (61% yield) m.p. 122°–123° C. (from ether/hexane).

Step B: Preparation of 1-methyl-10,11-dihydro-5H-dibenzo[a,d]cyclohepten-5-one.

Prepared from the above compound as described in Example 1B (65% yield). $\nu$max (Nujol) 1660 cm$^{-1}$ (c=o).

Step C: Preparation of 1-methyl-5H-dibenzo[a,d]cyclohepten-5-one.

Prepared from the above compound as described in Example 1C (20% yield), mp. 77°–80° C. (from acetone/hexane).

Step D: Preparation of 1,5-dimethyl-5H-dibenzo [a,d]cyclohepten-5-ol.

Prepared from the aboVe compound as described in example 1D (60% yield), m.p. 107°–109° (from ethyl acetate/hexane).

Step E: Preparation of 1,5-dimethyl-5-hydroxylamino-5H-dibenzo[a,d]cycloheptene.

Prepared from the above carbinol as in Example 1E. Yield 76%, m.p. 127°–130° C.

Step F: Preparation of a mixture of 1,5-dimethyl12-hydroxy-10,11-dihydro-5H-dibenzo[a,d]cyclohepten-5,10-imine and 5,9-dimethyl-12-hydroxy-10,11-dihydro-5Hdibenzo[a,d]cyclohepten-5,10-imine.

Prepared from the above hydroxylamine as in Example 1F, to give an orange solid in 50% yield. Two atroPisomers of each compound were present as adjudqed by 360MHZ nmr: δ (CDCl$_3$) 2.40 (0.3H), 2.55 (0.3H), 2.68 (0.15H), and 2.85 (0.15H) (CH of CH$_2$, J=18Hz).

Step G: Preparation of a mixture of 1,5-dimethyl-10,11-dihydro-5H-dibenzo[a,d]cyclohepten-5,10-imine and 5,9-dimethyl-10,11-dihydro-5H-dibenzo[a,d]cyclohepten-5,10-imine.

To the mixture from step F (800 mg) in glacial acetic acid (6 ml) was added powdered zinc (800 mg) and the mixture heated at 60° for 2hr, cooled, filtered and the cake washed with ether and water. Aqueous sodium hydroxide was added to the washings to pH 14 the ether layer separated, washed with brine, dried and evaporated. The residue was purified by column chromatography to give the product mixture as an oil (200 mg). which was used as such for step H.

Step H: Preparation of 1,5-dimethyl-10,11-dihydro-12-tert-butoxycaloryl-5H-dibenzo[a,d]cyclohepten-5,10,imine and 5,9-dimethyl-10,11-dihydro 12-tert-butoxy carbonyl-5H-dibenzo[a,d]cyclohepten 5,10imine.

The mixture from step G was treated with tert-butyl pyrocarbonate and the products separated as described in Example 1(H). to give the isomeric products A (105 mg) and B (27 mg) as oils.

Isomer A: nmr δ(CDCl$_3$) 2.59 (1H, d, J=14.4 Hz CH$_A$H$_B$); 3.61 (1H, dd CH$_A$H$_B$); 5.38 (1H, dd CH).

Isomer B: nmr δ(CDCl$_3$) 2.40 (1H, d, J=18 Hz, CH$_A$H$_B$); 3.25 (1H, dd, CH$_A$H$_B$); 5.39 (1H, d, J=8.6 Hz, CH).

Step I: Preparation of 1,5-dimethyl-10,11-dihydro-5H-dibenzo[a,d]cyclohepten-5,10-imine hydrochloride.

Isomer A from step H above (105 mg) was treated with dry HCl as in Example 1(I) to give 1,5-dimethyl-10,11-dihydro-5H-dibenzo[a,d]cycloheptene-5,10-imine hydrochloride (80 mg, 88%). m.p. 275°-278° C.

EXAMPLE 4

1,5-Dimethyl-10,11-dihydro-5H-dibenzo-[a,d]cyclohepten-5,10-imine.

Prepared from isomer B (Example (3H))as described in Example 1(I).m.p.>325° C. (dec).

EXAMPLE 5

3,5-Dimethyl-10,11-dihydro-5H-dibenzo-[a,d]cyclohepten-5,10-imine hydrochloride.

A solution of 412 mg (1.37 mmol) 3-bromo -10,11-dihydro-5-methyl-5H-dibenzo[a,d]-cyclohepten-5, 10-imine in 40 ml of ethyl ether was treated with 350 mg (0.64 mmol) of 1,3-bls(diphenylphosphino)propane nickel (II) chloride under an inert atomosphere. To the mixture was added a solution of methyl magnesium bromide in ether (3.0 M, 1.4 ml) and after the initial exothermic reaction had subsided the mixture was heated at 40° for 18 hours. TLC indicated incomplete reaction and an additional 3.0 ml of the Grignard reagent (3.0 M) was added portionwise and the mixture heated at reflux for 6 hours. Thereafter the reaction was cooled and quenched by the addition of 100 ml each of water and ether, the mixture transferred to a separatory funnel with an additional 300 ml of water and 200 ml of ammonium hydroxide. The mixture was shaken with 600 ml more ether and the layers allowed to separate. The ether layer was removed and dried (sodum sulfate) then concentrated under vacuum to afford 159 mg of a mixture which was partially purified by flash chromatography (ethyl acetate). Additional purification of the 3-methyl compound was achieved by preparative HPLC using a Waters PrepPak C-18 column. Homogeneous fractions were combined and concentrated to dryness, the material was flashed once more (chloroform, up to 5% methanol) and the hydrochloride salt of the title compound was prepared using ethanolic HCl: $C_{17}H_{17}N.HCl.0.4 H_2O$, 99.1% by HPLC. Anal. Calcd.: N, 5.02; C, 73.18; H, 6.60. Found : N, 5.03; C, 73.48; H, 6.63.

EXAMPLE 6

5-Methyl-3-phenyl-10,11-dihydro-5H-dibenzo-[a,d]cyclohepten-5,10-imine hydrochloride.

A mixture of 100 mg (0.33 mmol) of 3-bromo -10,11-dihydro-5-methyl-5H-dibenzo[a,d]-cyclohepten5,10-imine, 20 mg (0.017 mmol) of tetrakis(triphenylphosphine)palladium (0), 0.14 mL of triethylamine 60 mg (0.5 mmol) of phenylboronic acid and 3 mL of N N-dimethylformamide Was warmed to 100° C. under nitrogen atmosphere for 12 h. The mixture was concentrated by short path distillation under reduced pressure (0.05 mm bath temp 35° C.) to dryness. The nearly black residue was taken up in 10 mL of dilute aqueous ammonia (50 mL)) and extracted with three 50 mL portions of ethyl acetate. The combined extracts were washed with 10 mL of dilute aqueous ammonia, dried over magnesium sulfate, and concentrated to dryness. The residue was partially purified by flash chromatography with ethyl acetate as eluant, then appropriate fractions combined and further purified by preparative HPLC using a Whatman ODS-3 preparative column, eluting with 3% methanol 57% water and 40% acetonitrile (isochratic).

The homogeneous fractions (by HPLC) were combined, concentrated to dryness, and the residue partitioned between 50 mL of 0.5 N sodium hydroxide and 50 mL of chloroform. The residue from concentration of the chloroform extracts was dissolved in ether and acidified with 1 mL of 5.12 N ethanolic hydrochloric acid. The white precipitate (56 mg) was collected and dried to give the title compound. $C_{22}H_{19}N.HCl.0.5H_2O$; 99.95% by HPLC Anal. Calcd.: N, 4.09: C, 77.06; H, 6.17, Found : N. 4.38: C, 76.88; H 6.21.

EXAMPLE 7

7-Methyl-12,13-dihydro-7H-benzo[4,5]cyclohepta[1,2-a]naphthalen-7,12-imine

Step A: preparation of 7-hydroxy-7-methyl-7H-benzo[4,5]cyclohepta[1,2-a]naphthalene.

To a solution of 7H-benzo[4,5]cyclohepta[1,2-a]naphthalen-7-one (1.75 g, prepared by the method of Bergmann et al, *J. Org. Chem.*, 1963, 28, 3341) in dry tetrahydrofuran (40 ml) at 0° C. under nitrogen was added a solution of methyl lithium in diethyl ether (8 ml of 1.4M). After 90 minutes at 0° C. the reaction was quenched by the dropwise addition of water (20 ml) and the reaction mixture extracted into diethyl ether (2×75ml). dried ($Na_2SO_4$), filtered and the solvents removed under reduced pressure to give a light brown oil (1.9 g).

Step B: Preparation of 7-hydroxylamino-7-methyl-7H-benzo[4,5]cyclohepta[1,2-a]naphthalene Sodium acetate (5.7 g) and dichloroacetic acid (8.5 ml) were stirred together in dichloromethane (8.5 ml) at 0° C. for 5 minutes then hydroxylamine hydrochloride (4.8 g) added. After 1 h at room temperature more dichloromethane (17 ml) was added and after a further 30 minutes, the product from Example 7. Step A (1.9q) was added. After 1 h at room temperature the reaction mixture was poured into ice-water (200 ml) and washed with ammonia solution (70 ml). The organic layer was dried ($Na_2SO_4$), filtered and concentrated in vacuo to give the required product (2.04 g) as a colourless form. Spectral data were consistent with the proposed structure.

Step C: Preparation of 12-hydroxy-7-methyl-12,13-dihydro-7H-benzo[4,5]cyclohepta[1,2-a]naphthalen-7,12-imine and 12-hydroxy-7-methyl-12 13-dihydro-7H-benzo[4,5]cyclohepta[1,2-a]naphthalen-7-13-imine.

To xylene (100 ml) at reflux was added over a 20 minute period the hydroxylamine product from Example 7B (1.9 g) in xylene (100 ml) under nitrogen. After 30 minutes at reflux the reaction mixture was allowed to cool and the solvent removed under high vacuum to leave a brown residue. Trituration with ethyl acetate and filtration gave a white solid which was washed with methanol and dried in the vacuum oven to give, as a mixture of atropisomers, 12-hydroxy-7-methyl-12,13-dihydro-7H-benzo[4,5]cyclohepta[1,2-a]naphthalen-7,12-imine (0.72 g, 40%). The filtrate was concentrated in vacuo and the residue obtained purified by chromatography on silica gel with 25% ethyl acetate in hexane as eluent to give, as a white solid 12-hydroxy-7-methyl-12,13-dihydro-7H-benzo[4 5]cyclohepta[1,2-a]naphthalen-7,13-imine (0.41 g. 26%).

Step D: Preparation of 7-methyl-2,13-dihydro-7H-benzo[4,5]cyclohepta[1,2-a]naphthalen-7,12-imine hydrochloride.

12-Hydroxy-7-methyl-12,13-dihydro-7H-benzo[4,5-]cyclohepta[1,2-a]naphthalen-7,12-imine (0.25 g) and zinc dust (0.3 g) were heated together at 65° C. in glacial acetic acid (3 ml) for 14 h under an atmosphere of nitrogen. After this time the reaction mixture was filtered and the solvent removed in vacuo to leave a light brown oil This was dissolved in ether (40 ml) and washed with 1N sodium hydroxide solution (2×25 ml) then water (1×25 ml), dried ($Na_2SO_4$), filtered and concentrated under reduced pressure. The residue was dissolved in a 5 molar solution of hydrogen chloride in ethyl acetate then reconcentrated and dried under high vacuum to give 7-Methyl-12,13-dihydro-7H-benzo[4,5-]cyclohepta[1,2-a]naphthalen-7,12-imine hydrochloride (130 mg). m.p.>250° C. (dec.). p.m.r. (free base) (360MHz, DMSO-$d_6$) δ 2.03 (3H, s, $CH_3$), 3.09 (1H, d, J=16.9 Hz. H-11 endo), 3.77 (1H, dd, J=16.9 and 5.6 Hz, H-11 exo), 4.91 (1H, d, J=5.6Hz, H-10), 7.08 (3H, m, aromatics), 7.30–7.45 (3H m, aromatics), 7.50 (1H, d, J=8.6 Hz), 7.63 (1H, d, J=8.6 Hz), 7.72 (1H, d, J=7.9 Hz) and 7.81 (1H, d J=7.9 Hz). COSY spectra showed that H-6, H-7 and H-8 are in the 3 proton multiplet centred at δ 7.08, H-9 is at δ 7.33 and H-4 is at δ 7.50. Irradiation of the methyl group (δ 2.03) produced a n.O.e. to H-4 (δ 7.50) and H-6 (δ 7.08) while irradiation of H-10 gave a n.0.e. to H-9 (δ 7.33). Found: C, 73.81; H, 5.78; N, 4.19. $C_{20}H_{17}N.HCl.H_2O$ requires: C, 73.72; H. 6.19; N. 4.30%.

EXAMPLE 8

7-Methyl-12,13-dihydro-7H-benzo[4,5]cyclohepta[1,2-a]naphthalen-7,13-1mine hydrochloride.

12-Hydroxy-7-methyl-12,13-dihydro-7H-benzo[4,5-]cyclohepta[1,2-a]naphthalen-7,13-imine (Example 7, Step C. 300 mg) and zinc dust (370 mg) were heated together in glacial acetic acid (4 ml) at 65° C. for 14 h under an atmosphere of nitro9en. After this time the reaction mixture was filtered and the solvent removed in vacuo to leaVe a residue which was dissolved in ether (50 ml) and washed with 1M sodium hydroxide solution (1×25 ml). water (1×25 ml) then dried ($Na_2SO_4$), filtered and concentrated under vacuum. The white foam obtained was dissolved in a 5M solution of hydrogen chloride in ethyl acetate and the solvent removed in vacuo to leave as a white foam 7-methyl-12,13-dihydro-7H-benzo4,5]cyclohepta[1,2-a]naphthalen-7,13-imine hydrochloride (0.195 g). mp 208°–210° C.- p.m.r. (free base) (360MHz, DMSO-$d_6$) δ 2.02 (3H, s, $CH_3$), 2.85 (1H, d, J=16.8 Hz. H-11 endo). 3.54 (1H, dd, J=16.8 and 5.4 HZ, H-11 exo), 5.28 (1H. d, J=5.4 Hz, CH), 6.88 (1H, m), 7.05 (2H, m), 7.28 (2H, m), 7.40 (1H, dd, J=8.2, 8.0 Hz). 7.64 (1H, dd, J=8.3. 8.0 Hz), 7.81 (1H, d, J=8.2 Hz) and 7.86 (1H. d, J=8.3Hz). COSY spectra showed H-1 to be at δ 6.88 and H-16 to be at δ 7.86. Irradiation of H-10 (δ 5.28) gave a n.O.e. to H-16 (δ 7.86).

EXAMPLE 9

2,5-Dimethyl-10,11-dihydro-5H-dibenzo[a,d]cyclohepten-5,10-imine

2-Methyl-5H-dibenzo[a,d]cyclohepten-5-one (prepared by the method of Dunn et al, *J. Med. Chem.*, 1977, 20 1557) was converted as described in Example 1 Steps D-H. to a mixture of 2- and 8-methyl-5-methyl-12-tert-butoxycarbonyl-10,11-dihydro-5H-dibenzo [a,d]cyclohepten-5,10-imines. Separation of the regioisomers Was performed by reverse phase chromatography using a C-18 column eluting with $CH_3CN/H_2O$ (65:35). The 2-methyl regioisomer was deprotected as described in Example 1I to give 2,5-dimethyl-10,11-dihydro-5H-dibenzo[a,d]cyclohepten5,10imine hydrochloride. m.p. 185°–195° C. δ (360MHz, $CDCl_3$) 2.29 (3H, s, $CH_3$), 2.33 (3H, s, $CH_3$), 2.88 (1H, d, $CH_AH_B$), 3.99 (1H, dd, $CH_AH_B$), 5.25 (1H, d, CH) and 6.94–7.26 (7H, m, ArH). Found: C, 66.55 H, 6.16: N. 4.49. $C_{17}H_{17}N.2HCl$ requires: C. 66.24; H, 6.21; N, 4.54%. m/e 235 (M+). The assigned regiochemistry was confirmed by n.O.e. studies.

EXAMPLE 10

5,8-Dimethyl-10,11-dihydro-5H-dibenzo[a,d]cyclohepten-5,10-imine 5,8-Dimethyl-12-tert-butoxycarbonyl-10,11-dihydro5H-dibenzo[a,d]cyclohepten-5,10-imine (separated from the 2-methyl regioisomer as described in Example 9) was deprotected as described in Example 1H to give 5,8-dimethyl-10,11-dihydro-5H-dibenzo[a,d]cyclohepten-5,10-imine, m.p. 190°–195° C. δ (360MHz, $CDCl_3$) 2.20 (3H, s, $CH_3$), 2.31 (3H, s, $CH_3$), 2.85 (1H d, $CH_AH_B$), 3.94 (1H. dd, $CH_AH_B$), 5.28 (1H, d, CH) and 6.81-7.36 (7H, m, ArH). m/e 235 (M+). The assigned regiochemistry was confirmed by n.O.e. studies.

EXAMPLE 11

3-Methoxycarbonyl-5-methyl-10,11-dihydro-5H-dibenzo[a,d]cyclohepten-5,10-imine

Step A: Preparation of 3-carboxy-5-methyl-10,11-dihydro-5H-dibenzo[a,d]cyclohepten-5,10-imine In a 3 neck flask fitted with a thermometer, magnetic stirrer rubber septum and a gas inlet tube connected to a bubbler was dissolved 500 mg (1.66 mmole) of 3-bromo-5-methyl-10,11-dihydro-5H-dibenzo-[a,d]cyclohepten-5,10-imine in 10 ml of THF, previously distilled over sodium benzophenone ketyl. The solution, stirred at −78° C. under nitrogen atmosphere, was treated with 2.45 ml (4.15 meqs) of a 1.7M solution of tert-butyllithium in pentane. After stirring at −78° C. for 30 minutes the nitrogen was replaced by carbon dioxide generated from dry ice and sublimed, passing through a Drierite column en route to the reaction vessel. After a few minutes a copious white precipitate had formed and the cooling bath was removed. Stirring under $CO_2$ was continued at ambient temperature for two hours then 1 ml of water was added and the THF removed in vacuo. The residue was slurried in water (20 ml) until nearly a clear solution filtered and any undissolved solids washed with a small amount of water. The pH of the clear filtrate was carefully adjusted to 6.5 by addition of glacial acetic acid. The white solid which precipitated was washed with water, then with ether/acetonitrile mixtures to give the title compound, 280 mg (64%). PMR ($d_6$-DMSO) δ 1.87 (s. 3H $CH_3$), 2.66 (d, 1H, J=17Hz, C-11 exo H), 3.39 (dd, 1H, J=17 and 5.6Hz. C-11 endo H). 4.61 (d, 1H, J=5.3 Hz. C-10 H), 7.00–7.17 (m, 4H, aryl). 7.33 (d, 1H. J=6Hz, H1). 7.64 (dd, 1H, J=7.8 and 1.5Hz, H-2) and 7.83 (s, 1H. H-4).

Step B: Preparation of 3-methoxycarbonyl-5-methyl-10,11-dihydro-5H-dibenzo[a,d]cyclohepten-5,10-imine.

The 3-carboxy compound from Step A (265 mg 1 mmole) was suspended in 25 ml abs. $CH_3OH$, the mixture treated with 0.6 ml (5 mmol) boron trifluoride etherate, and the resulting solution was stirred at reflux for 18 hours. Removal of the solvent left a residue which was extracted with ether-saturated sodium bicarbonate. The combined ether extracts were washed (H2O, brine) and dried (Na2SO4) to afford 240 mg of 3-methoxycarbonyl-5-methyl-10,11-dihydro-5H-dibenzo[a,d]cyclohepten-5,10-imine. PMR (CDCl3) δ 1.99 (s, 3H, CH3), 2.63 (broad s, 1H, NH), 2.80 (d, 1H, J=17 Hz, C-11-exo H), 3.50 (dd, 1H, J=17, 5.4 Hz, C-11 endo-H), 3.90 (s, 3H, OCH3), 4.72 (d, 1H, J=5.4 Hz, C-10 H), 7.01–7.33 (m, 5H, aryl). 7.77 (dd, 1H, J=8 and 1.6 Hz, H-2) and 7.95 (d, 1H, J=1.7 Hz, H-4).

EXAMPLE 12

3-HYdroxymethyl-5-methyl-10,11-dihydro-5H-dibenzo-[a,d]cyclohepten-5,10-imine

A solution of 3-methoxycarbonyl-5-methyl-10,11-dihydro-5H-dibenzo[a,d]cyclohepten-5,10-imine (279 mg, 1.0 mmol) in a mixture of ether (20 ml) and dry THF (10 ml) was added dropwise with stirring, under nitorgen to a suspension containing 87 mg (2.3 mmole) of lithium aluminium hydride in 25 ml dry ether at 40° C. When the addition was complete the mixture was heated at 55° C. for 2 hours, then stirred at 25° C. for 18 hours. TLC (SiO2, CHCl3:CH3OH:NH4OH 90:10:1) indicated the reaction was complete. The mixture was chilled in an ice-bath and quenched by the dropwise addition of 10ml of saturated aqueous sodium potassium tartrate. After stirring for several hours the mixture was filtered and the while solid washed with water, then ether to give 3-hydroxymethyl-5-methyl-10,11-dihydro-5H-dibenzo[a,d] cyclohepten-5,10-imine (195 mg. 74%), mp 215°–217° C. Additional product could be obtained from the ether wash. The title compound had satisfactory PMR and high resolution spectra; for $C_{17}H_{17}NO.0.5H_2O$.

Anal. Calc'd: N. 5.38; C, 78.43; H, 6.97. Found : N, 5.28; C, 78.53; H, 6.87.

EXAMPLE 13

Tablet Preparation

Tablets containing 1.0, 2.0, 25.0 26.0 50.0 and 100.0 mg respectively of the following compounds are prepared as illustrated below:

5,7-Dimethyl-10,11-dihydro-5H-dibenzo[a,d]cyclohepten-5,10-imine 3,5-Dimethyl-10,11-dihydro-5H-dibenzo[a,d]cyclohepten-5,10-imine 3-Hydroxymethyl-5-methyl-10,11-dihydro-5H-dibenzo[a,d]cyclohepten-5.10-imine 3-Methoxycarbonyl-5-methyl-10,11-dihydro-5H-dibenzo[a,d]cyclohepten-5,10-imine

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound lactose and a portion of the corn starch are mixed and granulated to a 10% corn starch paste The resulting granulation is sieved dried and blended with the remainder of the corn starch and the magnesium stearate. The resulting granulation is then compressed into tablets containing 1.0 mg, 2.0 mg, 25.0 mg, 26.0 mg, 50.0 mg and 100.0 mg of active ingredient per tablet.

What is claimed is:

1. A compound of formula (I):

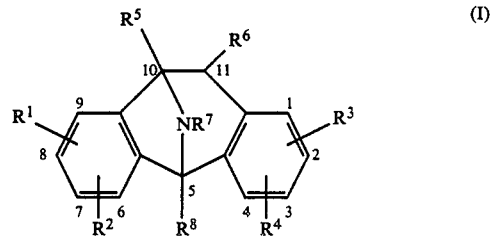

or a pharmaceutically acceptable salt thereof, wherein one of $R^1$, $R^2$, $R^3$ and $R^4$ represents a hydrocarbon having up to 18 carbon atoms, a group of formula —CO2R or substituted hydrocarbon wherein the substituent is selected from the group consisting of halogen, $C_{1-6}$ alkyl, phenyl, $C_{1-6}$ alkoxy, halo($C_{1-6}$)alkyl, hydroxy, amino, nitro, cyano, carboxy, $C_{1-6}$ alkoxycarbonyl, $C_{1-6}$ alkoxycarbonyl ($C_{1-6}$)alkyl, $C_{1-6}$ alkylcarbonyloxy, $C_{1-6}$ alkylcarbonyl and groups of formula —CONR$^a$R$^b$ and —NR$^a$. COR$^b$ in which R$^a$ and R$^b$ independently represent hydrogen or hydrocarbon having up to 18 carbon atoms and the remaining groups $R^1$, $R^2$, $R^3$ and $R^4$ are independently selected from the group consisting of hydrogen, hydrocarbon, substituted hydrocarbon wherein the substituents are as defined above, —CO2R, halogen, hydroxy and $C_{1-6}$ alkoxy or $R^1$ and $R^2$ or $R^3$ and $R^4$, when present on adjacent carbon atoms, may together represent the residue of a carbocyclic ring, the $R_1/R^2$ or $R^3/R^4$ carbon chain comprising from 2-6 carbon atoms; R represents a hydrocarbon having up to 18 carbon atoms or substituted hydrocarbon group wherein the substituents are as defined above; $R^5$ and $R^6$ are independently selected from the group consisting of hydrogen, hydrocarbon having up to 18 carbon atoms, hydroxy and fluoro; $R^7$ represents hydrogen of $C_{1-3}$ alkyl; and $R^8$ represents methyl or ethyl.

2. A compound of formula (II):

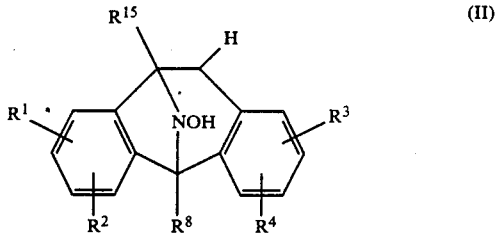

or a pharmaceutically acceptable salt thereof, wherein one of $R^1$, $R^2$, $R^3$ and $R^4$ represents a hydrocarbon having up to 18 carbon atoms, a group of formula —$CO_2R$ or substituted hydrocarbon wherein the substituent is selected from the group consisting of halogen, $C_{1-6}$ alkyl, phenyl, $C_{1-6}$ alkoxy, halo($C_{1-6}$)alkyl, hydroxy, amino, nitro, cyano, carboxy, $C_{1-6}$ alkoxycarbonyl, $C_{1-6}$ alkoxycarbonyl($C_{1-6}$)alkyl, $C_{1-6}$ alkylcarbonyloxy, $C_{1-6}$ alkylcarbonyl and groups of formula —$CONR^aR^b$ and —$NR^a$. $COR^b$ in which $R^a$ and $R^b$ independently represent hydrogen or hydrocarbon having up to 18 carbon atoms and the remaining groups $R^1$, $R^2$, $R^3$ and $R^4$ are independently selected from the group consisting of hydrogen, hydrocarbon, substituted hydrocarbon wherein the substituents are as defined above, —$CO_2R$, halogen, hydroxy and $C_{1-6}$ alkoxy or $R^1$ and $R^2$ or $R^3$ and $R^4$, when present on adjacent carbon atoms, may together represent the residue of a carbocyclic ring, the $R_1/R^2$ or $R^3/R^4$ carbon chain comprising from 2–6 carbon atoms; R represents a hydrocarbon having up to 18 carbon atoms or substituted hydrocarbon group wherein the substituents are as defined above; $R^8$ and represents methyl or ethyl and $R^{15}$ represents hydrogen or hydrocarbon having up to 18 carbon atoms.

3. The compound according to claim 1, wherein one of $R^1$ to $R^4$ is selected from the group consisting of $C_{1-6}$ alkyl, hydroxy($C_{1-6}$)alkyl, phenyl and $C_{1-6}$ alkoxycarbonyl, and the remaining groups $R^1$ to $R^4$ represent hydrogen or halogen.

4. The compound according to claim 1, wherein $R^1$ and $R^2$ or $R^3$ and $R^4$ together represent a carbocyclic ring, the $R^1/R^2$ or $R^3/R^4$ carbon chain of which comprises 3 or 4 carbon atoms.

5. The compound according to claim 1, wherein $R^5$ is selected from the group consisting of hydrogen, hydroxy and methyl and $R^6$ represents hydrogen or hydroxy.

6. The compound according to claim 1, wherein $R^7$ represents hydrogen and $R^8$ represents methyl.

7. The compound according to claim 1, wherein the hydrocarbon or a group of the formula —$CO_2R$ substituent, $R^1$ to $R^4$, is present at position 3 or 7 of the benzo rings wherein R is as defined therein.

8. The compound according to claim 1 selected from the group consisting of:
5,7-dimethyl-10,11-dihydro-5H-dibenzo[a,d]cyclohepten-5,10-imine;
5,9-dimethyl-10,11-dihydro-5H-dibenzo[a,d]cyclohepten-5,10-imine;
3,5-dimethyl-10,11-dihydro-5H-dibenzo[a,d]cyclohepten-5,10-imine;
1,5-dimethyl-10,11-dihydro-5H-dibenzo[a,d]cyclohepten-5,10-imine;
5-methyl-3-phenyl-10,11-dihydro-5H-dibenzo[a,d]cyclohepten-5,10-imine;
7-methyl-12,13-dihydro-7H-benzo[4,5]cyclohepta[1,2-a]naphthalen-7,12-imine;
7-methyl-12,13-dihydro-7H-benzo[4,5]cyclohepta[1,2-a]naphthalen-7,13-imine;
2,5-dimethyl-10,11-dihydro-5H-dibenzo[a,d]cyclohepten-5,10-imine;
5,8-dimethyl-10,11-dihydro-5H-dibenzo[a,d]cyclohepten-5,10-imine;
3-methoxycarbonyl-5-methyl-10,11-dihydro-5H-dibenzo-[a,d]cyclohepten-5,10-imine;
3-hydroxymethyl-5-methyl-10,11-dihydro-5H-dibenzo-[a,d]cyclohepten-5,10-imine;
and salts thereof.

9. A pharmaceutical composition for the treatment of convulsion or cerebral ischemia induced neurodegeneration comprising an effective anticonvulsant and antineurodegenerative amount of a compound according to claim 1 together with a pharmaceutically acceptable carrier or excipient.

10. A method for the treatment of convulsions which comprises administering to a patient in need of such treatment an effective amount of a compound according to claim 1.

11. A method for the treatment of cerebral ischemia induced neurodegeneration diseases which comprises administering to a patient in need of such treatment an effective amount of a compound according to claim 1.

* * * * *